(12) United States Patent
Moore

(10) Patent No.: US 10,111,743 B2
(45) Date of Patent: Oct. 30, 2018

(54) WRAPPING CLIP FOR SECURING A FLEXIBLE LINE TO ANOTHER OBJECT

(71) Applicant: Southwest Research Institute, San Antonio, TX (US)

(72) Inventor: Andrew R. Moore, San Antonio, TX (US)

(73) Assignee: SOUTHWEST RESEARCH INSTITUTE, San Antonio, TX (US)

(*) Notice: Subject to any disclaimer, the term of this patent is extended or adjusted under 35 U.S.C. 154(b) by 23 days.

(21) Appl. No.: 15/216,241

(22) Filed: Jul. 21, 2016

(65) Prior Publication Data

US 2018/0021123 A1  Jan. 25, 2018

(51) Int. Cl.
*A61F 2/08* (2006.01)
*A61B 17/04* (2006.01)
*A01K 91/04* (2006.01)
*F16G 11/00* (2006.01)
*F16G 11/14* (2006.01)

(52) U.S. Cl.
CPC ............... *A61F 2/08* (2013.01); *A01K 91/04* (2013.01); *A61B 17/0401* (2013.01); *F16G 11/00* (2013.01); *F16G 11/146* (2013.01); *A61B 2017/0414* (2013.01); *A61B 2017/0417* (2013.01); *A61F 2002/0894* (2013.01)

(58) Field of Classification Search
CPC .............................. A61F 2/08; A61B 17/0401
USPC .......... 606/74, 139, 158, 151, 157, 219, 232
See application file for complete search history.

(56) References Cited

U.S. PATENT DOCUMENTS 4,444,187 A * 4/1984 Perlin ................ A61B 17/1227
606/158
2006/0004410 A1* 1/2006 Nobis ................ A61B 17/0401
606/232
2016/0296741 A1* 10/2016 Patterson ........... A61M 39/1011

* cited by examiner

*Primary Examiner* — Vy Bui
(74) *Attorney, Agent, or Firm* — Livingston Law Firm

(57) ABSTRACT

A securing device for securing a flexible line to another object. The clip has a working end and a clip end, the former for attachment to the other object and the latter for securing the line. The clip end has two loops and a locking clip. The two loops extend in opposite directions away from the locking clip, and are connected by a crossbar which is perpendicular to and against the locking clip. The locking clip is formed from two parallel shafts, closely spaced together. The line is secured by wrapping it at least twice around the loops, then up over the crossbar and down into the locking clip.

6 Claims, 2 Drawing Sheets

WRAPPING CLIP FOR SECURING A FLEXIBLE LINE TO ANOTHER OBJECT

TECHNICAL FIELD OF THE INVENTION

This invention relates to hardware for attaching flexible lines to other objects, and more particularly to rings and clips that prevent the line from slipping without use of a knot.

BACKGROUND OF THE INVENTION

It is often desired to secure a flexible line to another object. Many different kinds of knots have been devised for this purpose.

However, it is sometimes desired to accomplish the same result without tying a knot. Knots can tend to be difficult to undo, can damage the line, and it can be difficult to exactly control the location of the knot.

Various "no knot" hardware devices have been developed for various applications. For example, fishing hooks and lures have been developed, such as the one described in US Pub. No. 2005/0274054. An on-line search for "no knot fishing" will illustrate many such devices.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to a wrapping clip that is especially useful for securing an artificial muscle to a termination point. However, as is evident, the clip is also a general solution to securely attaching various types of flexible lines to another object without requiring knots.

Thus, in addition to an artificial muscle, the "line" to be attached may be any flexible line, such as thread, yarn, string, rope, cord, polymer filament, or the like. These flexible lines, and others, are generally referred to herein as "lines".

Figure 1:
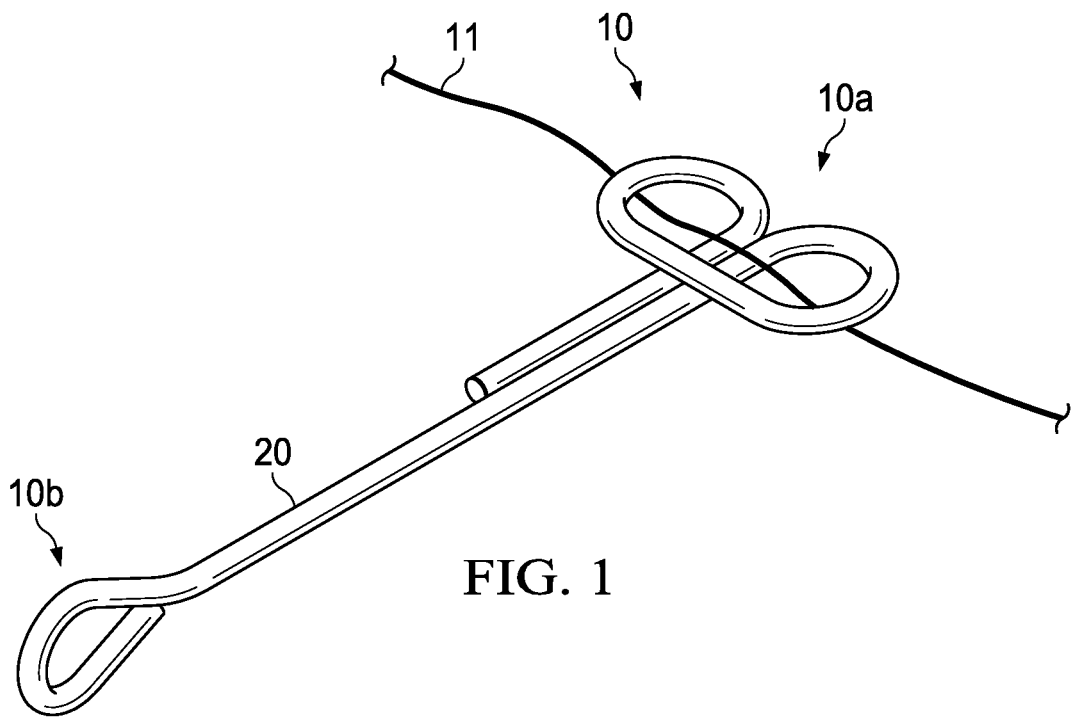
FIG. 1 is a top perspective view of the wrapping clip, and also showing a line in position prior to being wrapped and clipped into place in the clip.
Figure 2:
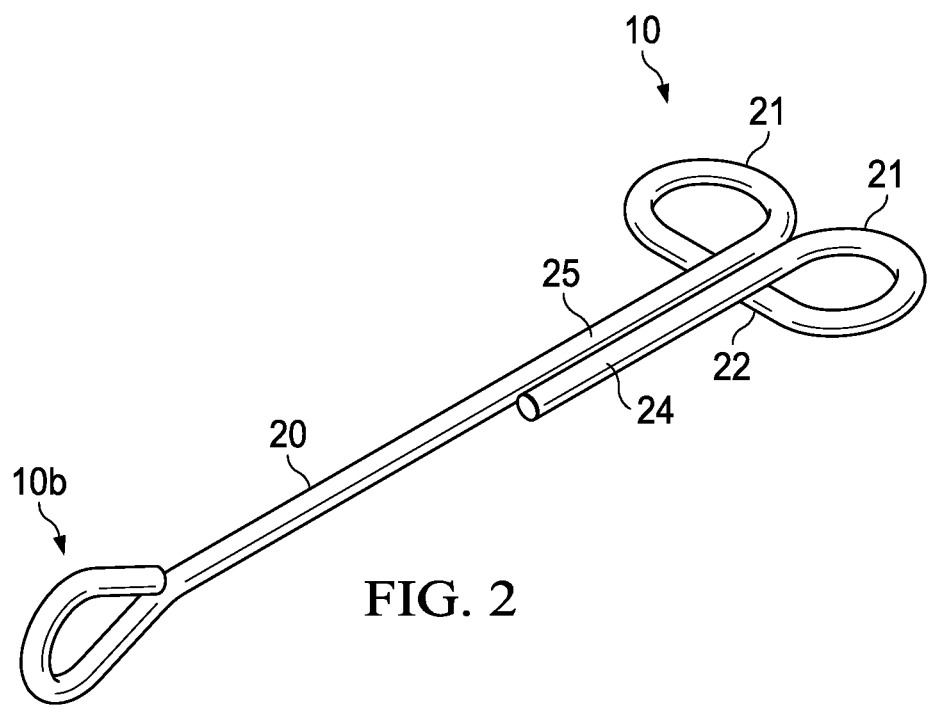
FIG. 2 is a bottom perspective view of the wrapping clip.

FIGS. 1 and 2 are top and bottom perspective views, respectively, of one embodiment of a wrapping clip 10 for securing a flexible line 11 to another object. Clip 10 is configured to frictionally retain flexible line 11, without any need for a knot to attach and fix line 11 to clip 10.

As depicted, clip 10 has a clip end 10a at one end. Its other end is a "working end" 10b, here configured as a closed loop. A main shaft 20 connects the clip end 10a to the working end 10b.

In FIG. 1, line 11 is shown in position for the beginning of the method of securing line 11 to clip 10. As explained below in connection with FIGS. 3-5, several additional steps are required to complete the connection of line 11 to clip 10.

Clip end 10a is configured to affix to a segment of a flexible line 11. Once the flexible line 11 is inserted into clip end 10a, such as in the manner described below, clip 10 is immobile on that segment of line 11. Generally, clip end 10a has two continuous loops 12 configured to accept a length of line 11 in an interwoven or interlaced fashion. Once line 11 is connected to clip 10, if line 11 is pulled, the friction exerted against portions of clip end 10a causes line 11 to resist being pulled through clip 10.

More specifically, clip end 10a has a first loop 21 that curves away from the end of shaft 20 and then curves back toward shaft 20 to a point between the clip end and working end of shaft 20. This first loop 21 continues to the second loop 21, which curves away from shaft 20 and then curves back toward the end of shaft 20. The end of the first loop 21 and the beginning of the second loop 21 from a crossbar 22 that is perpendicular to the main shaft 20.

The end of the second loop then extends to begin a secondary shaft 24, which runs parallel to and against the main shaft 20, to form a locking clip 25. Thus, the locking clip 24 is an extension of parallel wires from an end of each of the two loops where the loops are adjacent each other.

The two loops 21 are generally in the same plane as each other. The end of the first loop and the beginning of the second loop form a crossbar 22 that is atop and against locking clip 24. The crossing of crossbar 22 over locking clip 24 prevents the loops 21 from being completely flat. The two loops 21 are generally orthogonal, in two different directions, relative to the main shaft 20 and locking clip 24. The crossbar 22 is substantially straight.

The overall structure of clip 10 is generally flat—all elements of clip 10 are in a plane that is no more than double the diameter of the material from which clip 10 is made. This flat characterization of clip 10 does not include any structures, such as the closed eyelet of FIGS. 1 and 2, placed at the working end 10b.

The working end 10b is configured to secure clip 10, and hence line 11, to another object. The details of the working end 10b may vary. Alternatives to a closed loop are a hook, a threaded rod, an eyelet, or another clover clip. The working end 10b could be directly attached to another object, such as by welding, in which case the working end 10b may simply be an end point of shaft 20. In still other applications, the working end 10b may be integrated with some other structure, so that clip 10 may be used to attach a flexible line to that structure.

Formation of Clip from Single Length of Wire

Clip 10 may be formed from a single length of wire. For purposes of this description, the material from which clip 10 is formed is referred to as "wire". The wire may be a single core wire or rod, or may formed from multiple wires, such as braided wire or cable. The wire may be solid or hollow.

Various materials, which are malleable (bendable), but substantially rigid once formed into the desired shape, may be used. Depending on the application, some flexibility of clip 10 once formed may be desired.

Typical materials of the wire are various metals. Some applications may call for clip 10 to be electrically conductive. If electrical conductivity is not required, clip 10 may be formed from a plastic rod, molded, or printed with a three-dimensional printer, directly into shape rather than being bent from a straight rod.

The diameter of the wire may vary depending on the application. Often the desired application will call for a smooth and thin clip, in which case, appropriate wire may be selected.

The wire from which clip 10 is formed extends down from the working end 10b to form a main shaft 20. At about the midpoint or further down the main shaft 20 from the working end 10b, the wire is bent into a half-cloverleaf shape as shown in FIGS. 1 and 2. The half-cloverleaf shape is characterized by two loops 21 and a crossbar 22 as described above.

After being bent into the two loops 21 and crossbar 22 that form the half-cloverleaf of the clip end 10a, the wire is run parallel to and against main shaft 20. This results in two parallel portions of the wire, which form a locking clip 25. As explained below, these two parallel portions of the wire abut or are sufficiently close together so that the line 11 may be snugly passed between them. Depending on the application and the diameter of line 11, the wire from which clip 10 is formed may require some flexibility to allow line 11 to be inserted within locking clip 25 or under crossbar 22.

Method of Securing Line to Clip

As stated above, line 11 can be securely attached to the wrapping clip 10 without tying any knots. Various techniques of wrapping line 11 around loops 21 and through locking clip 25 may be used. But in general, the method comprises at least two wraps around the loops 21 followed by slipping the line 11 through the two parts (main shaft and secondary shaft) of the locking clip 25.

One attachment method can be summarized as "wrap-wrap-snap", but this shorthand really only describes Steps 3 and 4 of the method described below. The attachment may be performed at any place along line 11, not necessarily at an end.

The following method is described from the perspective of FIG. 1. The clip end 10a is distal to (down from) the perspective of the user, and the crossbar 22 is on top of the clip 10.

Step 1. Slide line 11 down shaft 20, along locking clip 25, and into the space between the locking clip 25 and under the crossbar 22. This step is shown in FIG. 1.

Step 2. Slide clip 10 along the line 11 until it is in the desired position on line 11.

Figure 3:
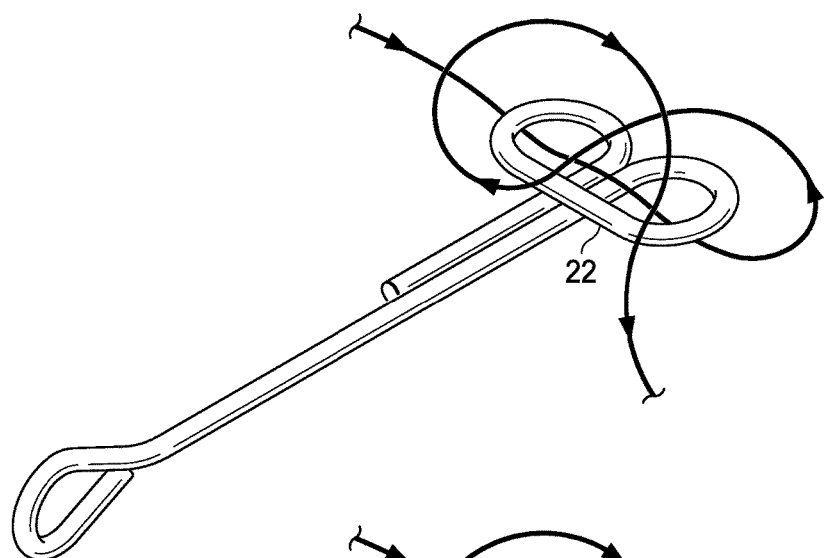
FIG. 3 illustrates a line being wrapped twice around the loops of the wrapping clip.

Step 3. As shown in FIG. 3, with the crossbar 22 facing up (shown as on top of the clip in the top view of FIG. 1), take the end of the line that will be under tension and wrap it at least twice over the loops 21. It is preferred that the line is wrapped around both the left and right loops 21, but experimentation has shown that it doesn't matter whether it is wrapped around the left loop twice, the right loop twice, or if it is wrapped around the left and right loops once each. The direction of the wrap should be up and over the crossbar 22, then back under and between the loops 21.

Figure 4:
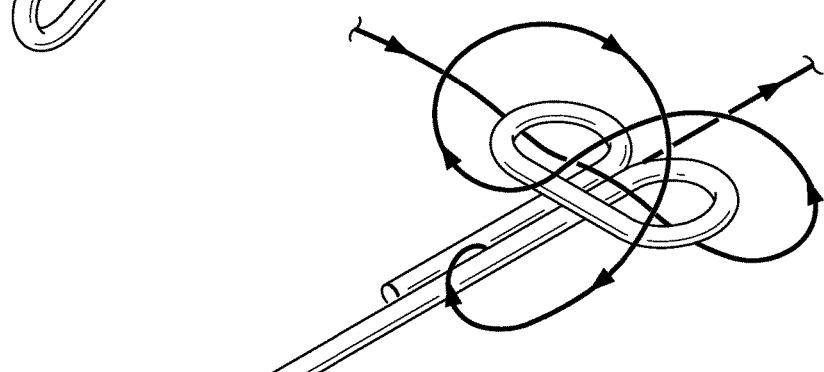
FIG. 4 illustrates the line of FIG. 3, now wrapped and being clipped into place.

Step 4. As shown in FIG. 4, continue in the same wrapping motion for at least two wraps around the loops 21. Next, bring the line 11 up (toward the user) over the crossbar 22 and then down between the two parallel portions of clip 10 that form locking clip 25 from the direction of the working end 10b. Slide line 11 down (away) into the locking clip 25. Pull line 11 toward the clip end 10a until line 11 clicks into place. At this point the line 11 is secured, and it may be placed under tension.

Figure 5:
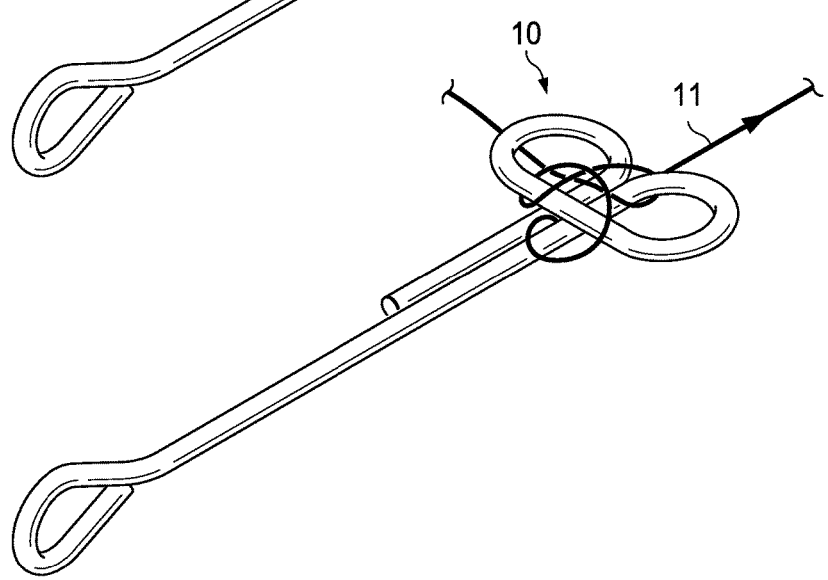
FIG. 5 illustrates the line of FIG. 4 after being wrapped and clipped into the clip.

Step 5. If desired, cut off any excess line from the tag (non tensioned) end. With the excess line removed, the clip 10 and line 11 will appear as shown in FIG. 5. Alternatively, if clip 10 is placed in the middle of a line, there is no tag end to cut off.

Once secured, line 11 will not come loose from the clip 10. Various points of contact of line 11 with the clip end 10a contribute to the frictional retention of line 11 by clip 10.

However, if line 11 is desired to be removed from clip 10, line 11 may be brought out of the locking clip 25 and unwrapped from out of the clip end 10a. In other words, clip 10 is "reversible" in the sense that line 11 can be removed and adjusted or otherwise reused. Similarly, even if both ends of the line 11 are secured, the line 11 may be loosened from clip 10 and adjusted along line 11.

Applications

Clip 10 is especially useful when the "flexible line" 11 is an artificial muscle. For artificial muscle applications, clip 10 solves the problem of how to "terminate" the artificial muscle to an attachment point. In other words, some means is needed to attach artificial muscles to other structures in order to properly characterize them. Various mechanical and electrical terminations have been attempted, such as by tying knots or crimping the muscle fibers with terminal rings. However, knots are problematic because the coiled muscle was prone to damage during tying, and it is difficult to control the length. Terminal rings are bulky, and a crimp does not always hold the muscle securely.

Clip 10 is advantageous for terminating artificial muscles because it is compact, low cost, and can be attached rapidly to artificial muscles in a repeatable fashion.

Clip 10 is particularly useful for electrically conductive coiled polymer artificial muscles (not to be confused with electro-active polymer muscles, or EPAMs), where the muscle termination needs to be mechanically sound and electrically conductive. In this case, clip 10 is made from a conductive material.

However, electrical connectivity is not always required, as in the case of non-conductive coiled monofilament artificial muscles. If electrical conductivity is not required for a particular application, the clover clip may be constructed of a non-conductive material such as those described above.

It is preferred that clip 10 be attached to an artificial muscle material prior to coiling the muscle, as the attachment procedure may distort or damage the coils.

Another example application of clip 10 is for attaching fishing line to fishing hooks and lures ("fishing devices"). An advantage of clip 10 is that the fishing device can be more easily positioned on the line prior to wrapping and snapping it in place. This is in contrast to other so-called "no-knot" fishing devices, which require that a loop be formed prior to attachment.

Fishing devices or any other devices may integrate the working end 10b of clip 10 to form a device with an integrated clip 10. Then, the device may be attached in the middle of a line after other devices have already been attached to the end. This is not possible with traditional single-eyelet fishing devices.

For all applications, clip 10 may be easier than knot tying for people with limited dexterity. The "wrap-wrap-snap" method described above is a simple, continuous motion that does not require as much fine manipulation as knot-tying, which inherently requires the passing of one end of the line through a loop.

Other applications for clip 10 may include rope tie-downs, jewelry making, and clothing tie-offs such as for shoe laces, dresses, corsets, etc.

What is claimed is:

1. A securing device configured to facilitate the securing of a flexible line to another object, the device comprising:
   a single continuous length of wire, shaped to form the following elements:

a main shaft having a working end and a clip end;

a first loop extending from the main shaft in a first direction;

wherein the first loop is formed as a continuous loop having a first loop beginning at the clip end of the main shaft, curving away from the main shaft, and curving back toward the main shaft to a first loop end;

second loop extending from the main shaft in a second direction and in the same plane as the first loop;

wherein the second loop is formed as a continuation of the wire, beginning from where the first loop ends at the main shaft, extending past the main shaft, and curving back toward the beginning of the first loop, such that the second loop has a second loop end tightly adjacent to the first loop beginning, such that when the line is wrapped between the first loop and the second loop, there is a first point of contact between the line and the clip that contributes to frictional retention of the line in the clip a locking clip formed as straight secondary shaft extending from the second loop end, parallel to and tightly adjacent to the main shaft such that when the line is wedged between the main shaft and the secondary shaft, there is a second point of contact between the line and the clip that contributes to frictional retention of the line in the clip;

wherein the working end of the main shaft ends at the lowermost extremity of the securing device and the first and second loop form the uppermost extremity of the securing device.

2. The device of claim 1, wherein the main shaft, first loop, second loop, and secondary shaft are formed from bending a single piece of material.

3. The device of claim 1, wherein the main shaft, first loop, second loop, and secondary shaft are formed by three dimensional printing.

4. The device of claim 1, wherein the main shaft, first loop, second loop, and secondary shaft are formed by molding.

5. The device of claim 1, wherein the first loop end and the second loop beginning form a straight crossbar across and against the main shaft and secondary shaft.

6. The device of claim 1, wherein the main shaft, first loop, second loop, and secondary shaft are generally in the same plane, other than where first loop end and second loop beginning cross over the main shaft and secondary shaft.

\* \* \* \* \*